(12) United States Patent
Elowe et al.

(10) Patent No.: US 10,836,697 B2
(45) Date of Patent: Nov. 17, 2020

(54) PROCESS FOR THE PREPARATION OF LIGHTLY-BRANCHED HYDROPHOBES AND THE CORRESPONDING SURFACTANTS AND APPLICATIONS THEREOF

(71) Applicant: Dow Global Technologies LLC, Midland, MI (US)

(72) Inventors: Paul R. Elowe, Midland, MI (US); Wanglin Yu, Pearland, TX (US); Brad C. Bailey, Midland, MI (US); Michael L. Tulchinsky, Midland, MI (US); Andre B. Argenton, Midland, MI (US); Daniel J. Arriola, Midland, MI (US); Jerzy J. Klosin, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/218,945

(22) Filed: Dec. 13, 2018

(65) Prior Publication Data

US 2019/0112250 A1 Apr. 18, 2019

Related U.S. Application Data

(62) Division of application No. 14/901,057, filed as application No. PCT/US2014/042887 on Jun. 18, 2014, now Pat. No. 10,196,336.

(60) Provisional application No. 61/840,765, filed on Jun. 28, 2013.

(51) Int. Cl.
| | | |
|---|---|---|
| *C07C 45/50* | (2006.01) | |
| *C11D 1/14* | (2006.01) | |
| *C11D 3/16* | (2006.01) | |
| *C07C 303/24* | (2006.01) | |
| *C07C 2/32* | (2006.01) | |
| *C07C 29/141* | (2006.01) | |
| *B01J 31/22* | (2006.01) | |
| *C07C 7/04* | (2006.01) | |
| *C07C 31/125* | (2006.01) | |
| *C07C 41/01* | (2006.01) | |
| *C07C 303/20* | (2006.01) | |
| *C07C 309/04* | (2006.01) | |

(52) U.S. Cl.
CPC ......... *C07C 45/505* (2013.01); *B01J 31/2213* (2013.01); *C07C 2/32* (2013.01); *C07C 7/04* (2013.01); *C07C 29/141* (2013.01); *C07C 31/125* (2013.01); *C07C 41/01* (2013.01); *C07C 45/50* (2013.01); *C07C 303/20* (2013.01); *C07C 303/24* (2013.01); *C07C 309/04* (2013.01); *C11D 1/143* (2013.01); *C11D 1/146* (2013.01); *C11D 3/168* (2013.01); *B01J 31/223* (2013.01); *B01J 2231/20* (2013.01); *B01J 2531/48* (2013.01); *C07C 2531/14* (2013.01); *C07C 2531/18* (2013.01); *C07C 2531/22* (2013.01)

(58) Field of Classification Search
CPC .................................................. C07C 45/505
See application file for complete search history.

(56) References Cited

U.S. PATENT DOCUMENTS

| | | | |
|---|---|---|---|
| 5,849,960 A | 12/1998 | Singleton et al. | |
| 6,087,309 A | 7/2000 | Vinson et al. | |
| 6,133,209 A | 10/2000 | Rath et al. | |
| 6,150,322 A | 11/2000 | Singleton et al. | |
| 6,222,077 B1 | 4/2001 | Singleton | |
| 6,482,789 B1 | 11/2002 | Kvietok et al. | |
| 6,566,565 B1 | 5/2003 | Murray et al. | |
| 6,765,106 B2 | 7/2004 | Fenouil et al. | |
| 7,102,038 B2 | 9/2006 | Murray et al. | |
| 7,148,375 B2 | 12/2006 | Edwards et al. | |
| 7,335,802 B2 | 2/2008 | Ayoub et al. | |
| 7,462,730 B2 | 12/2008 | Raney et al. | |
| 7,781,390 B2 | 8/2010 | Singleton et al. | |
| 7,871,973 B1 | 1/2011 | Singleton et al. | |
| 7,888,307 B2 | 2/2011 | Singleton et al. | |
| 7,994,369 B2 | 8/2011 | Scheibel et al. | |
| 8,044,249 B2 | 10/2011 | Scheibel et al. | |
| 8,211,949 B2 | 7/2012 | Varineau et al. | |
| 8,232,431 B2 | 7/2012 | Price et al. | |
| 9,938,214 B1 * | 4/2018 | Harvey | C07C 2/34 |

(Continued)

FOREIGN PATENT DOCUMENTS

| | | |
|---|---|---|
| EP | 0364012 | 1/1993 |
| EP | 1325899 | 7/2003 |

(Continued)

OTHER PUBLICATIONS

Lipska-Quinn A. E., et al., "Thermal Degradation of Rice Straw and its Components" Jan. 1, 1982 (22 pgs).

(Continued)

*Primary Examiner* — Shawquia Jackson
(74) *Attorney, Agent, or Firm* — Brooks, Cameron & Huebsch, PLLC

(57) ABSTRACT

Processes to prepare lightly branched surfactant products comprise combining at least one olefin and a coordination-insertion catalyst under conditions such that at least one oligomer product is formed. The surfactant products comprise a main carbon chain containing an average of between 0.5 and 2.5 branches, wherein more than 50% of the branches are ethyl branches, wherein the branches are located more than one carbon away from each end of the main carbon chain in more than 20% of surfactant product molecules.

16 Claims, 7 Drawing Sheets

(56) References Cited

U.S. PATENT DOCUMENTS

2005/0107628 A1     5/2005   Roper et al.
2014/0330056 A1    11/2014   Klosin et al.

FOREIGN PATENT DOCUMENTS

GB           2451325      1/2009
WO       2005085321      9/2005

OTHER PUBLICATIONS

International Search Report and Written Opinion for related PCT Application PCT/US2014/042887, dated Aug. 29, 2014 (11 pgs).

\* cited by examiner (formula IV)

formula (V)

formula (VI)

formula (VII)

formula (VIII)

formula (IX)

formula (X)

Formula (IX)

PROCESS FOR THE PREPARATION OF LIGHTLY-BRANCHED HYDROPHOBES AND THE CORRESPONDING SURFACTANTS AND APPLICATIONS THEREOF

CROSS-REFERENCE TO RELATED APPLICATION

This application is a divisional application from U.S. application Ser. No. 14/901,057, filed Dec. 27, 2015, and published as U.S. Publication No. 2016-0130206 A1 on May 12, 2016, which claims priority to International Patent Application No. PCT/US2014/042887, filed Jun. 18, 2014, and published as WO Publication No. WO 2014/209711 on Dec. 31, 2014, which claims priority to U.S. Provisional Application No. 61/840,765, filed Jun. 28, 2013, all of which are hereby incorporated herein by reference in their entireties.

FIELD

The invention relates to processes for the manufacture of lightly-branched hydrophobes, and their corresponding non-ionic and anionic surfactants.

BACKGROUND

Surfactant molecules generally comprise a water-soluble moiety (hydrophile) and an oil-soluble moiety (hydrophobe). Various hydrophilic groups, such as polyoxyethylene, polysaccharide, quaternary ammonium, amine oxide, sulfate, sulfonate, sulfosuccinate, carboxylic, and the like, are attached to an alkyl, alkenyl, or alkaryl hydrophobe that usually contains 8 to 20 carbon atoms through different linkage chemistries. The hydrophobe structure affects the properties, performance, biodegradability, toxicity, and therefore the application of the surfactants. Hydrophobes may be derived from natural oils and fats, which are typically linear. Linear hydrophobes are favorable in affording ready biodegradability of surfactants. However, they are limited in providing key performance features of surfactants, such as high solubility, easy handling and good wetting.

Hydrophobes can also be synthesized from petrochemical or coal-derived raw materials. Synthetic hydrophobes include the linear versions that are functionally equivalent to the linear hydrophobes derived from natural oils and fats. One advantage of synthetic hydrophobes is the flexibility of creating various branching structures by using different chemistries and processes. In general, branched hydrophobes help afford surfactants with better handling properties, less stable foam, and enhanced wettability, which are highly desirable features in many applications. The highly branched structure of the hydrophobe however may cause poor surfactant biodegradability. It is believed that a lightly branched hydrophobe may provide a favorable balance between high performance and ready biodegradability for the corresponding surfactant.

Current processes for generating lightly branched surfactants require multiple steps to obtain the desired branching. In addition, such processes typically require the use of more than one starting monomer. Thus, there is a need for a process for preparing surfactants with the same ability to reduce surface tension as the surfactants produced by the current processes, but in fewer steps. Furthermore, there is a need for a process for preparing surfactants from only one starting monomer.

BRIEF SUMMARY

In one aspect, a process is provided comprising combining at least one olefin and at least one coordination-insertion catalyst and, optionally, an alpha-olefin, wherein the coordination-insertion catalyst is a metal-ligand complex wherein the metal is selected from zirconium, hafnium and titanium, and has an ethylene/octene reactivity ratio up to 20 at an operating reactor temperature, and a kinetic chain length up to 20 monomer units; under conditions such that at least one oligomer product is formed. The oligomer product includes a main carbon chain containing an average of between 0.5 and 2.5 branches, wherein more than 50% of the branches are ethyl branches, wherein the branches are located on average more than one carbon away from each end of the main carbon chain in more than 20% of oligomer product molecules, wherein the branches are situated at a second carbon relative to an unsaturated end of the main carbon chain in less than 40% of the oligomer product molecules, and wherein the oligomer product contains greater than 50% vinyl olefin. The process further comprises fractionating the oligomer product to produce a fractionated oligomer product, such that the average carbon number of the fractionated oligomer product is between 8 and 28; and hydroformylating the fractionated oligomer product to produce an aldehyde product or sulfonating the fractionated oligomer product to produce a sulfonated surfactant product.

In another aspect, a process comprises combining at least one olefin and at least one coordination-insertion catalyst and, optionally, an alpha-olefin, wherein the coordination-insertion catalyst is a metal-ligand complex wherein the metal is selected from zirconium, hafnium and titanium, and has an ethylene/octene reactivity ratio up to 20 at an operating reactor temperature, and a kinetic chain length up to 20 monomer units; under conditions such that at least one oligomer product is formed. The oligomer product includes a main carbon chain containing an average of between 0.5 and 2.5 branches, wherein more than 50% of the branches are ethyl branches, wherein the branches are located on average more than one carbon away from each end of the main carbon chain in more than 20% of oligomer product molecules, wherein the branches are situated at a second carbon relative to an unsaturated end of the main carbon chain in less than 40% of the oligomer product molecules, and wherein the oligomer product contains greater than 50% vinyl olefin. The process further comprises fractionating the oligomer product to produce a fractionated oligomer product, such that the average carbon number of the fractionated oligomer product is between 8 and 28; hydroformylating the fractionated oligomer product to produce an aldehyde product; and hydrogenating the aldehyde product to produce an alcohol product.

In another aspect, an alcohol product is provided, comprising a main carbon chain containing an average of between 0.5 and 2.5 branches, wherein more than 50% of the branches are ethyl branches, wherein the branches are located more than one carbon away from each end of the main carbon chain in more than 20% of alcohol product molecules.

In yet another aspect, a lightly branched surfactant product is provided, comprising a main carbon chain containing an average of between 0.5 and 2.5 branches, wherein more than 50% of the branches are ethyl branches, wherein the branches are located more than one carbon away from each end of the main carbon chain in more than 20% of surfactant product molecules.

DETAILED DESCRIPTION

Figure 1:
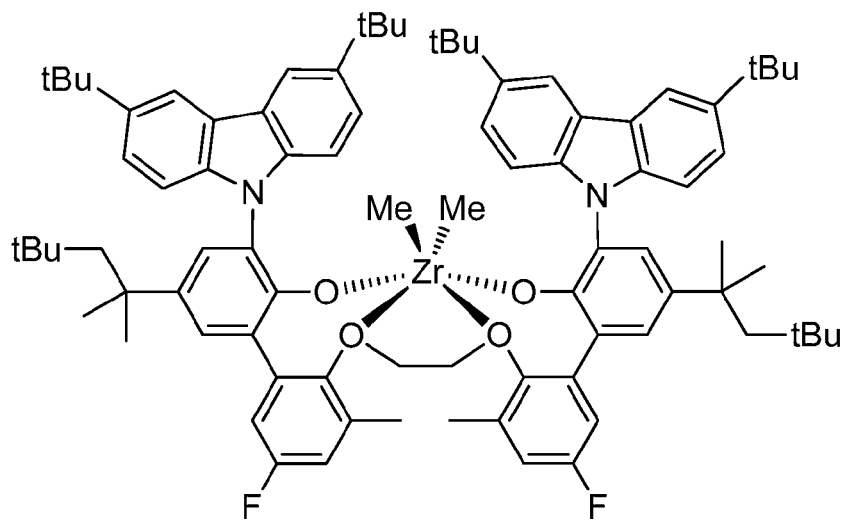
FIG. 1 is a formula drawing of a coordination-insertion catalyst of the formula 2',2'''-(ethane-1,2-diylbis(oxy))bis(3-(3,6-di-tert-butyl-9H-carbazol-9-yl)-5'-fluoro-3'-methyl-5-(2,4,4-trimethylpentan-2-yl)-[1,1'-biphenyl]-2-ol)-zirconiumdimethyl.
Figure 2:
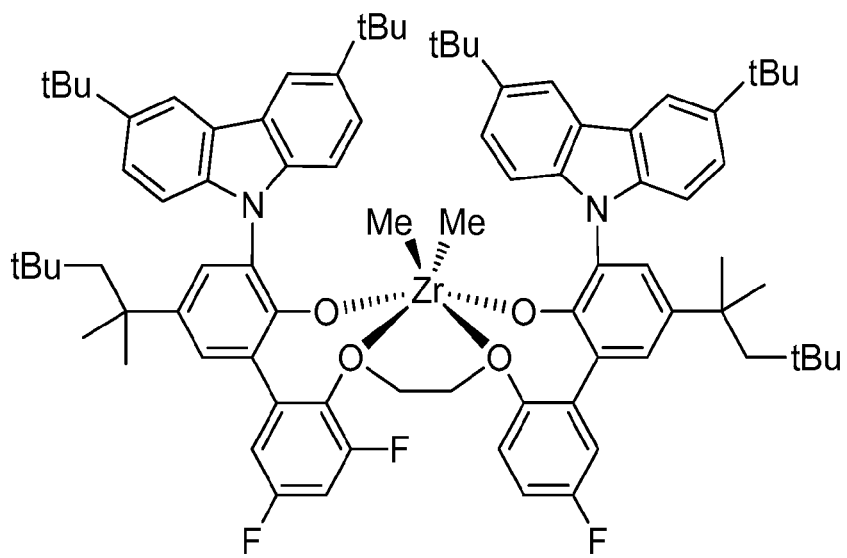
FIG. 2 is a formula drawing of a coordination-insertion catalyst of the formula 3-(3,6-di-tert-butyl-9H-carbazol-9-yl)-2'-(2-((3'-(3,6-di-tert-butyl-9H-carbazol-9-yl)-5-fluoro-2'-hydroxy-5'-(2,4,4-trimethylpentan-2-yl)-[1,1'-biphenyl]-2-yl)oxy)ethoxy)-3',5'-difluoro-5-(2,4,4-trimethylpentan-2-yl)-[1,1'-biphenyl]-2-ol-zirconiumdimethyl.
Figure 3:
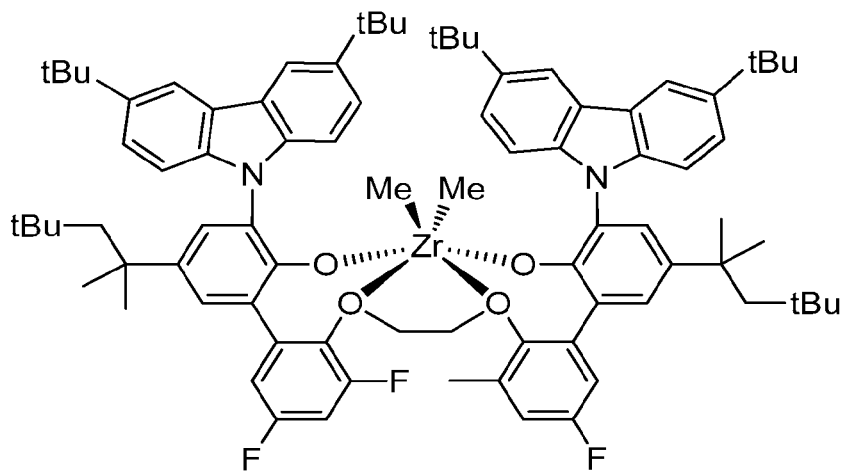
FIG. 3 is a formula drawing of a coordination-insertion catalyst of the formula 3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol-zirconiumdimethyl.
Figure 4:
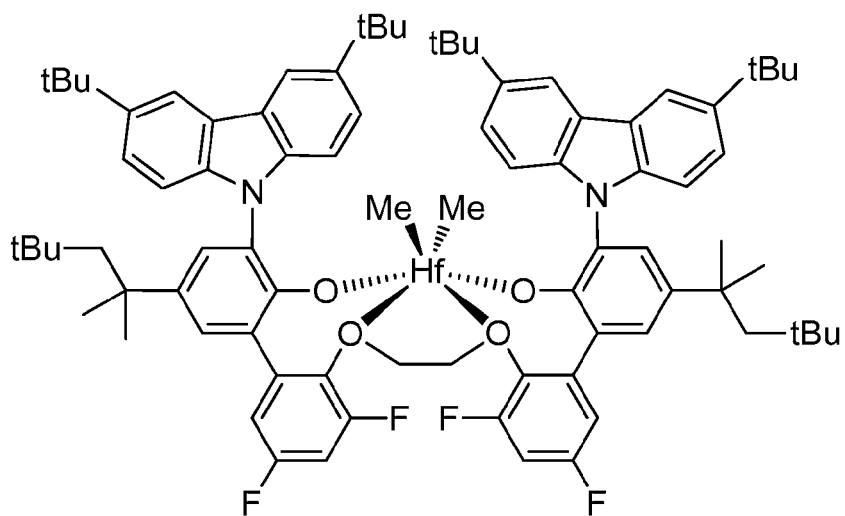
FIG. 4 is a formula drawing of a coordination-insertion catalyst of the formula 2',2'''-(ethane-1,2-diylbis(oxy))bis(3-(3,6-di-tert-butyl-9H-carbazol-9-yl)-3',5'-difluoro-5-(2,4,4-trimethylpentan-2-yl)-[1,1'-biphenyl]-2-ol)-hafniumdimethyl.
Figure 5:
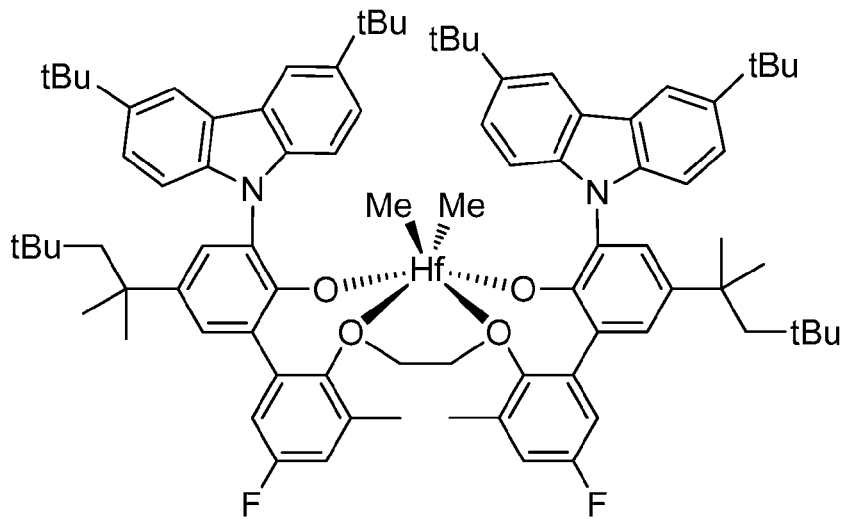
FIG. 5 is a formula drawing of a coordination-insertion catalyst of the formula 2',2'''-(ethane-1,2-diylbis(oxy))bis(3-(3,6-di-tert-butyl-9H-carbazol-9-yl)-5'-fluoro-3'-methyl-5-(2,4,4-trimethylpentan-2-yl)-[1,1'-biphenyl]-2-ol)-hafniumdimethyl.
Figure 6:
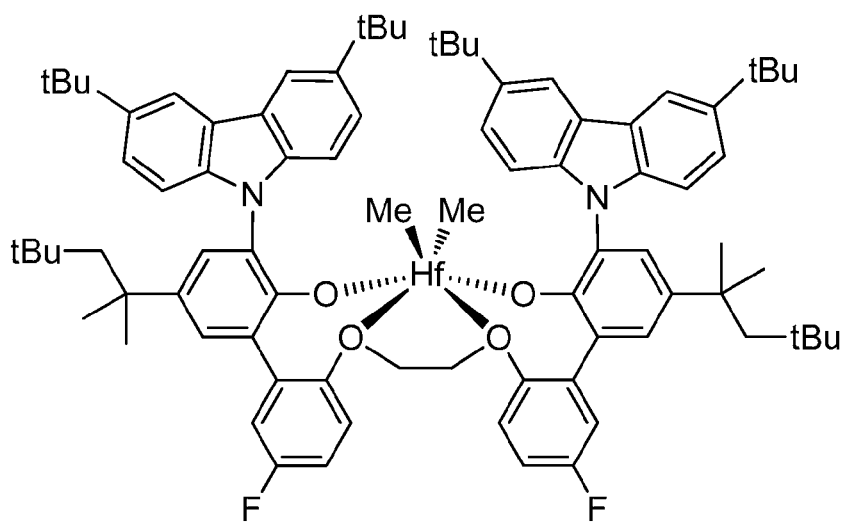
FIG. 6 is a formula drawing of a coordination-insertion catalyst of the formula 6',6'''-(ethane-1,2-diylbis(oxy))bis(3-(3,6-di-tert-butyl-9H-carbazol-9-yl)-3'-fluoro-5-(2,4,4-trimethylpentan-2-yl)-[1,1'-biphenyl]-2-ol)-hafniumdimethyl.
Figure 7:
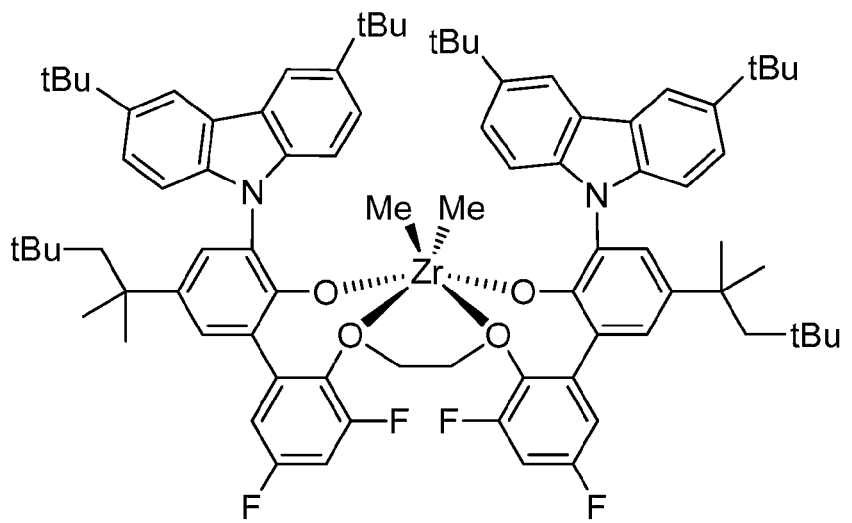
FIG. 7 is a formula drawing of a coordination-insertion catalyst of the formula 2',2'''-(ethane-1,2-diylbis(oxy))bis(3-(3,6-di-tert-butyl-9H-carbazol-9-yl)-3',5'-difluoro-5-(2,4,4-trimethylpentan-2-yl)-[1,1'-biphenyl]-2-ol)-zirconiumdimethyl.

This invention provides a new process to produce lightly mid-branched olefins and alcohols as hydrophobes for surfactants, in which majority of the mid-branched groups is ethyl or higher alkyl, at least 50% of the branches are ethyl or higher alkyl, and there is no (<1%) terminal isopropyl type of branch.

The present process is advantageous in that it generates lightly branched surfactants for improved performance while maintaining ready biodegradability. Furthermore, the process provides significant cost advantage since (1) it generates the desired branching structure in one step to the oligomer, without further processing, and (2) can be prepared from only one monomer, such as ethylene.

The process comprises several steps: (1) formation of a lightly branched ethylene oligomer, (2) formation of a hydrophobe (in some embodiments, the hydrophobe is the ethylene oligomer itself), and (3) formation of a surfactant product. The lightly branched hydrophobes may be prepared first via ethylene oligomerization, generating a mixture of lightly branched olefins, which are then (1) converted to alcohols, then (2a) alkoxylated to generate nonionic surfactants, (2b) first ethoxylated or alkoxylated then sulfated to generate anionic ethoxysulfate or alkoxysulfate surfactants or (2c) sulfated to generate sulfated surfactants. The lightly branched hydrophobe may also comprise the oligomeric lightly branched olefin which is then (3) directly converted to anionic sulfonated surfactants via sulfonation, respectively.

The preparation of the oligomer involves (1) oligomerization of the olefin using a catalyst and appropriate process conditions to make oligomeric products that approximate a Schulz-Flory distribution of oligomeric products, and (2) fractionation to obtain the desired fraction to generate the hydrophobe or fractionated oligomer product, such that the average carbon number of the fraction is between C8 and C28. Preferably, the average carbon number of the fractionated oligomer product may be between C8 and C10, between C8 and C12, between C8 and C14, between C10 and C12, between C10 and C14, between C10 and C16, between C12 and C14, between C12 and C16, between C14 and C16, between C14 and C18, or between C16 and C18. When a carbon number is given, it means a distribution of molecules averaging that carbon number. For example C12 means a distribution of molecules averaging twelve carbon atoms.

The starting olefin may be ethylene alone, or a proportion of an alpha-olefin comonomer may be included along with ethylene. The starting olefin may also be any terminal olefin, for example, linear olefins. If an alpha-olefin is to be included, it may be selected from, in non-limiting example, linear alpha-olefins having from 3 to 12 carbons, such as propylene, 1-butene, 1-pentene, 1-hexene, 1-heptene, 1-octene, 1-nonene, 1-decene, 1-undecene, 1-dodecene, and combinations thereof.

The starting olefin mixture may contain three types of olefins: olefins with vinyl groups, olefins with vinylidene groups, and olefins with vinylene groups. The olefin mixture may comprise greater than 50% olefins with vinyl groups, preferably between about 70% and 80% olefins with vinyl groups. The olefin mixture may also comprise about 20% olefins with vinylidene groups and about 5% olefins with vinylene groups. Preferably vinylidene group is 1,1-ethenediyl.

Notwithstanding the above, it is preferred that only a minor amount of alpha-olefin is included, if any. That amount preferably ranges from 0 to 30 mol %; more preferably from 0 to 25 mol %; still more preferably from 0 to 20 mol %; yet more preferably from 0 to 10 mol %; and most preferably from 0 to 5 mol %. The amount of added alpha-olefin is most commonly preferred to be 0 mol % because added alpha-olefins tend to be more costly than the spectrum of alpha-olefins that are created in-situ. While ethylene feed streams often have a small fraction (less than 1 mol %) of alpha-olefin monomer impurities such as propylene, it is expected that such would have no significant detrimental effect on process operation or oligomer properties.

In the inventive process the selected starting olefin or olefins, is/are contacted with a suitable coordination-insertion catalyst. As the term is used here, "coordination-insertion" means that the catalysts are capable of consecutively inserting unsaturated monomers, with the result that previously unsaturated carbons in the monomers and the oligomer become the backbone of a new oligomer. This catalyst may be selected, in one embodiment, from a wide variety of metal-ligand complexes. Those skilled in the art will be aware that catalyst performance varies with process temperature and also may vary with reaction mixture composition and conversion. Preferred catalysts are those exhibiting an activity level of 100,000 grams of oligomer per gram of catalyst metal (g/g cat). Also preferred are catalysts capable of producing a chain termination rate that results in product oligomer of a desired molecular weight and having a high fraction, preferably at least 25%, more preferably at least 50%, and most preferably at least 75%, of vinyl groups.

Kinetic chain length is also important in identifying particularly suitable catalysts for the present invention. Kinetic chain length is defined as the average number of monomeric repeat units incorporated by a catalyst before a chain transfer or chain growth terminating reaction.

Examples of suitable coordination-insertion catalysts may generally include, in certain non-limiting embodiments, metal-ligand complexes including any of the metals zirconium, hafnium, or titanium, and preferably zirconium or hafnium. Among these catalysts may be certain metallocene catalysts, including certain constrained geometry catalysts, and bis-phenylphenoxy catalysts, provided that the selected catalyst meets the ethylene/octene reactivity ratio and kinetic chain length requirements as defined hereinabove.

The metallocene compounds useful herein are cyclopentadienyl derivatives of titanium, zirconium, and hafnium. These metallocenes (e.g., titanocenes, zirconocenes and hafnocenes) may be represented by the following formula:

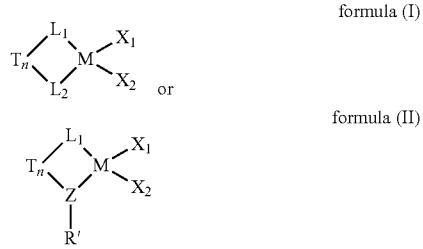

formula (I)

formula (II)

wherein M is the metal center, and is a Group 4 metal, preferably titanium, zirconium or hafnium;

T is an optional bridging group which, if present, in preferred embodiments is selected from dialklsilyl, diarylsilyl, dialkylmethyl ethylenyl (—$CH_2$—$CH_2$—) or hydrocarbylethylenyl wherein one, two, three or four of the hydrogen atoms in ethylenyl are substituted by hydrocarbyl, where hydrocarbyl can be independently $C_1$ to $C_{16}$ alkyl or phenyl, tolyl, xylyl and the like, and when T is present, the catalyst represented can be in a racemic or a meso form;

$L_1$ and $L_2$ are the same or different cyclopentadienyl, indenyl, tetrahydroindenyl or fluorenyl rings, optionally substituted, that are each bonded to M, or $L_1$ and $L_2$ are the same or different cyclopentadienyl, indenyl, tetrahydroindenyl or fluorenyl, which are optionally substituted, in which any two adjacent R groups on these rings are optionally joined to form a substituted or unsubstituted, saturated, partially unsaturated, or aromatic cyclic or polycyclic substituent;

Z is nitrogen, oxygen or phosphorus;

R' is a cyclic linear or branched $C_1$ to $C_{40}$ alkyl or substituted alkyl group; and $X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand.

Among the metallocene compounds which can be used in this invention are stereorigid, chiral or asymmetric, bridged or non-bridged, or so-called "constrained geometry" metallocenes. See, for example and methods for preparation, U.S. Pat. Nos. 4,892,851; 5,017,714; 5,132,281; 5,155,080; 5,296,434; 5,278,264; 5,318,935; 5,969,070; 6,376,409; 6,380,120; 6,376,412; WO-A-(PCT/US92/10066); WO 99/07788; WO-A-93/19103; WO 01/48034; EP-A2-0 577 581; EP-A1-0 578 838: WO 99/29743, and also the academic literature, e.g., "The Influence of Aromatic Substituents on the Polymerization Behavior of Bridged Zirconocene Catalysts," Spaleck, W., et al., *Organometallics* 1994, Vol. 13, pp. 954-963; "ansa-Zirconocene Polymerization Catalysts with Annelated Ring Ligands-Effects on Catalytic Activity and Polymer Chain Lengths," Brintzinger, H., et al., *Organometallics* 1994, Vol. 13 pp. 964-970; "Constrained geometry complexes—Synthesis and applications," Braunschweig, H., et al., *Coordination Chemistry Reviews* 2006, 250, 2691-2720; and documents referred to therein.

The process uses as catalysts a particular subset of the bis-phenylphenoxy compounds described in US20110282018. These are termed metal-ligand complex catalysts that combine a transition metal center and any of a wide variety of bis-phenylphenoxy-containing ligands conforming to formula (III), provided that the following limitations are met. First, the bridge, L, between the Z moieties is from 2 atoms to 8 atoms in length. Second, the Z moieties may be selected independently from oxygen, sulfur, phosphorus ($C_{1-40}$)hydrocarbylene, and nitrogen ($C_{1-40}$)hydrocarbylene. Third, the ligand has a halogen atom located in at least one of the positions on the benzene rings in the $R^{1a}$ and/or $R^{1b}$ position of formula (III), i.e., at a position, or positions, that is/are ortho to the bridged Z moieties. The term "halogen atom" means a fluorine atom radical (F), chlorine atom radical (Cl), bromine atom radical (Br), or iodine atom radical (I). Preferably each halogen atom independently is a Br, F, or Cl radical, and more preferably a F or Cl radical. Fourth, the metal M is preferably selected from zirconium (Zr), hafnium (Hf), and titanium (Ti), and more preferably is either Zr or Hf.

The members of the catalyst family defined are generally convenient to prepare and may operate efficiently and over a wide thermal operating range, in some non-limiting embodiments withstanding temperatures exceeding 200° C. Such catalysts may, themselves, be of effectively any molecular weight ($M_w$), but in certain non-limiting embodiments preferably range from 200 Daltons (Da) to 5,000 Da. Preparation may include, in non-limiting embodiments, construction of a suitable ligand structure followed by its reaction with a salt of the desired transition metal, which effects the desired metal-ligand complexation. Additional and highly detailed preparation information may be found in, e.g., the previously referenced US20110282018; US Serial Number PCT/US2012/0667700, filed Nov. 28, 2012, claiming priority to U.S. Provisional Application 61/581, 418, filed Dec. 29, 2011; and U.S. Ser. No. 13/105,018, filed May 11, 2011, Publication Number 20110282018, claiming priority to U.S. Provisional Application 61/487,627, filed Mar. 25, 2011. Those skilled in the art will recognize that similar and analogous processes may be used to prepare other useful bis-phenylphenoxy compounds falling within the given general definition.

In certain embodiments, such suitable catalysts may generally include, in more specific but non-limiting embodiments, metal-ligand complexes of formula (III)

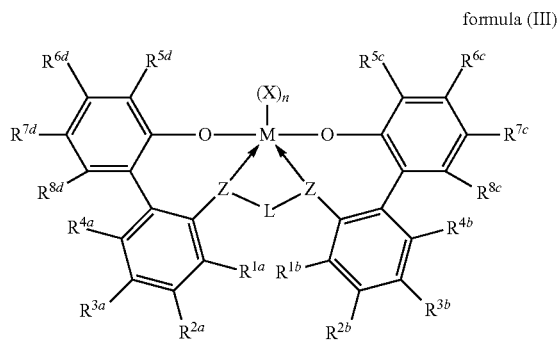

formula (III)

wherein M is titanium, zirconium, or hafnium, each independently being in a formal oxidation state of +2, +3, or +4; n is an integer of from 0 to 3, wherein when n is 0, X is absent; each X independently is a monodentate ligand that is neutral, monoanionic, or dianionic, or two X are taken together to form a bidentate ligand that is neutral, monoanionic, or dianionic; X and n are selected such that the metal-ligand complex is, overall, neutral; each Z is independently O, S, N($C_1$-$C_{40}$)hydrocarbyl, or P($C_1$-$C_{40}$)hydrocarbyl; L is ($C_1$-$C_{40}$)hydrocarbylene or ($C_1$-$C_{40}$)heterohydrocarbylene, wherein the ($C_1$-$C_{40}$)hydrocarbylene has a portion that comprises a 2- to 8-atom linker backbone linking the Z moieties and the ($C_1$-$C_{40}$)heterohydrocarbylene has a portion that comprises a 2- to 8-atom linker backbone linking the Z moieties, wherein each atom of the 2- to 8-atom linker of the ($C_1$-$C_{40}$)heterohydrocarbylene independently is a carbon atom or a heteroatom, wherein each heteroatom independently is O, S, S(O), S(O)$_2$, Si($R^C$)$_2$, Ge($R^C$)$_2$, P($R^P$), or N($R^N$), wherein independently each $R^C$ is unsubstituted ($C_1$-$C_{18}$)hydrocarbyl or the two $R^C$ are taken together to form a ($C_2$-$C_{19}$)alkylene, each $R^P$ is unsubstituted ($C_1$-$C_{18}$)hydrocarbyl; and each $R^N$ is unsubstituted ($C_1$-$C_{18}$)hydrocarbyl, a hydrogen atom or absent; $R^{1a}$, $R^{1b}$, or both is a halogen atom; $R^{2a}$ and $R^{2b}$ independently is a hydrogen, ($C_1$-$C_{40}$)hydrocarbyl, ($C_1$-$C_{40}$)heterohydrocarbyl, N($R^N$)$_2$, NO$_2$, O$R^C$, S$R^C$, Si($R^C$)$_3$, Ge($R^C$)$_3$, CN, CF$_3$, F$_3$CO, halogen atom; and each of the others of $R^{1a}$, $R^{2a}$, $R^{1b}$, and $R^{2b}$ independently is a hydrogen, ($C_1$-$C_{40}$)hydrocarbyl, ($C_1$-$C_{40}$)heterohydrocarbyl, N($R^N$)$_2$, NO$_2$, O$R^C$, S$R^C$, Si($R^C$)$_3$, CN, CF$_3$, F$_3$CO or halogen atom; each of $R^{3a}$, $R^{4a}$, $R^{3b}$, $R^{4b}$, $R^{6c}$, $R^{7c}$, $R^{8c}$, $R^{6d}$, $R^{7d}$, and $R^{8d}$ independently is a hydrogen atom; ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, O$R^C$, S$R^C$, NO$_2$, CN, CF$_3$, RCS(O)—, RCS(O)$_2$—, (RC)$_2$C=N—, RCC(O)O—, RCOC(O)—, RCC(O)N(R)—, (RC)$_2$NC(O)— or halogen atom; each of $R^{5C}$ and $R^{5d}$ is independently a ($C_6$-$C_{40}$)aryl or ($C_1$-$C_{40}$)heteroaryl; and each of the aforementioned aryl, heteroaryl, hydrocarbyl, heterohydrocarbyl, hydrocarbylene, and heterohydrocarbylene groups is independently unsubstituted or substituted with one or 5 more substituents $R^S$; and each $R^S$ is independently a halogen atom, polyfluoro substitution, perfluoro substitution, unsubstituted ($C_1$-$C_{18}$)alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the $R^S$ are taken together to form an unsubstituted ($C_1$-$C_{18}$)alkylene, wherein each R independently is an unsubstituted ($C_1$-$C_{18}$)alkyl.

A wide variety of additional substitution may be present at all other carbons of the at least four phenyl rings included within the catalyst of formula (III) or such may have simply hydrogen. Some examples of preferred $R^{5c}$ and $R^{5d}$ substituents include 3,5-di(tertiary-butyl)phenyl; 3,5-diphenylphenyl; 1-naphthyl, 2-methyl-1-naphthyl; 2-naphthyl; 1,2,3,4-tetrahydronaphthyl; 1,2,3,4-tetrahydro-naphth-5-yl; 1,2,3,4-tetrahydronaphth-6-yl; 1,2,3,4-tetrahydroanthracenyl; 1,2,3,4-tetrahydroanthracen-9-yl; 1,2,3,4,5,6,7,8-octahydroanthracenyl; 1,2,3,4,5,6,7,8-octahydroanthracen-9-yl; phenanthren-9-yl; 1,2,3,4,5,6,7,8-octahydrophenanthren-9-yl; 2,3-dihydro-1H-inden-6-yl; naphthalene-2-yl; 1,2,3,4-tetrahydronaphthalen-6-yl; 1,2,3,4-tetrahydronaphthalen-5-yl; anthracen-9-yl; 1,2,3,4-tetrahydroanthracen-9-yl; 1,2,3,4,5,6,7,8-octahydro-anthracen-9-yl; 2,6-dimethylphenyl; 2,6-diethylphenyl; 2,6-bis(1-methylethyl)phenyl; 2,6-diphenyl-phenyl; 3,5-dimethylphenyl; 3,5-bis(tri-fluoromethyl)phenyl; 3,5-bis(1-methylethyl)phenyl; 3,5-bis(1,1-dimethylethyl)phenyl; 3,5-diphenyl-phenyl); 2,4,6-trimethylphenyl; and 2,4,6-tris(1-methylethyl)phenyl); 1-methyl-2,3-dihydro-1H-inden-6-yl; 1,1-dimethyl-2,3-dihydro-1H-inden-6-yl; 1-methyl-1,2,3,4-tetrahydro-naphthalen-5-yl; 1,1-dimethyl-1,2,3,4-tetrahydronaph-thalen-5-yl. 1,2,3,4-tetrahydroquinolinyl; isoquinolinyl; 1,2,3,4-tetrahydroisoquinolinyl; carbazolyl; 1,2,3,4-tetrahydrocarbazolyl; 1,2,3,4,5,6,7,8-octahydrocarbazolyl; 3,6-di(tertiary-butyl)-carbazolyl; 3,6-di(tertiary-octyl)-carbazolyl; 3,6-diphenylcarbazolyl; 3,6-bis(2,4,6-trimethylphenyl)-carbazolyl; 3,6-di(tertiary-butyl)-carbazol-9-yl; 3,6-di(tertiary-octyl)-carbazol-9-yl; 3,6-diphenylcarbazol-9-yl; 3,6-bis(2,4,6-trimethylphenyl)-carbazol-9-yl; quin-olin-4-yl; quinolin-5-yl; quinolin-8-yl; 1,2,3,4-tetrahydroquinolin-1-yl; isoquinolin-1-yl; isoquinolin-4-yl; iso-quinolin-5-yl; isoquinolin-8-yl; 1,2,3,4-tetrahydroisoquinolin-2-yl; 1H-indol-1-yl; 1H-indolin-1-yl; 9H-carbazol-9-yl; 1,2,3,4-tetrahydrocarbazolyl-9-yl; 1,2,3,4,5,6,7,8-octahydrocarbazolyl-9-yl; 4.6-bis(1,1-dimethylethyl)pyri dine-2-yl; 4,6-diphenylpyridin-2-yl; 3-phenyl-1H-indol-1-yl; 3-(1,1-dimethylethyl)-1H-indol-1-yl; 3,6-diphenyl-9H-carbazol-9-yl; 3,6-bis[2',4',6'-tris(1,1-dimethylphenyl)]-9H-carbazol-9-yl; 3,6-bis(1,1-dimethyl-ethyl)-9H-carba-zol-9-yl.

In more particular embodiments, the catalyst may be selected from the compounds represented by formulas (IV) to (X), shown in FIGS. 1-7. Additional moieties denoted by abbreviations include Me (methyl) and t-Bu (tert-butyl).

In carrying out the process of the invention it is desirable that the contact between the olefin(s) and the coordination-insertion catalyst occur in a continuously-fed backmixed reactor zone. As the term is used herein, "backmixed reactor zone" refers to an environment wherein a reaction product is intermingled with unconverted reactor feeds. A continuous stirred tank reactor is preferred for this purpose, while it is noted that plug-flow reactors are specifically designed to prevent back-mixing. However, a loop reactor can accomplish a variable degree of backmixing by recycling a portion of reactor effluent to the feed of a plug-flow zone, with the recycle ratio moderating the degree of backmixing. Thus, plug-flow reactors are non-preferred, while a loop reactor with a plug flow zone is preferred. In the inventive process backmixing ensures reaction of already-produced oligomers with new feedstock, e.g., ethylene. It is this continuous contact that enables the oligomers to become branched via repeated olefin insertion.

Conditions under which the contact occurs in the continuously-fed, backmixed reactor zone may include a temperature desirably ranging from 0° C. to 250° C., more desirably from 25° C. to 200° C., and most desirably from 50° C. to 180° C.; an ethylene partial pressure desirably ranging from 15 psi (pounds per square inch, 103 kilopascals, kPa) to 500 psi (3450 kPa), more desirably from 30 psi (207 kPa) to 300 psi (2070 kPa), and most desirably from 50 psi (345 kPa) to 200 psi (1380 kPa); and a residence time desirably ranging from 1 minute (min) to 120 min, more desirably from 5 min to 60 min, and most desirably from 10 min to 30 min. A reactor system may be comprised of many low residence time reaction zones or a few high residence time reaction zones. Nonetheless, those skilled in the art will easily understand that alteration of parameters may be employed for reasons of convenience, alteration of yield, avoidance of undesirable side products or degradation, and the like.

In order to prepare the homo-oligomers or co-oligomers of the invention, the starting olefin and/or the selected alpha-olefin monomer(s) is/are fed into a suitable reactor, for batch, semi-continuous, or continuous production, wherein such olefin(s) will come into contact with the catalyst. In the case of preparation of co-oligomers, it is noted that the ethylene/alpha-olefin reactivity ratio is distinct for any given catalyst and provides a methodology to determine the amount of alpha-olefin that will be required to attain a targeted co-oligomer composition. Reactivity ratios may be determined using well known theoretical techniques or empirically derived from actual polymerization data. Suitable theoretical techniques are disclosed, for example, in B. G. Kyle, *Chemical and Process Thermodynamics*, $3^{rd}$ ed., Prentice-Hall (1999) and in Soave, Giorgio. "Equilibrium constants from a modified Redlich-Kwong equation of state", *Chemical Engineering Science*, Vol. 27, Issue 6, June 1972, pp. 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201, USA.

The metal-ligand complex discussed above is rendered catalytically active by contacting it to, or combining it with, the activating co-catalyst or by using an activating technique such as those that are known in the art for use with metal-based olefin polymerization reactions. Suitable activating co-catalysts for use herein include alkyl aluminums; polymeric or oligomeric alumoxanes (also known as aluminoxanes); neutral Lewis acids; and non-polymeric, non-coordinating, ion-forming compounds, including but not limited to the use of such compounds under oxidizing conditions. A suitable activating technique may be bulk electrolysis. Combinations of one or more of the foregoing activating co-catalysts and/or techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Alumoxanes and their preparations are described in, for additional understanding, U.S. Pat. No. 6,103,657. Examples of preferred polymeric or oligomeric alumoxanes are methylalumoxane, triisobutylaluminum-modified methylalumoxane, and isobutylalumoxane. Such may be employed such that the ratio of total number of moles of the one or more metal-ligand complexes of formula (III) to total number of moles of activating co-catalyst is preferably from 1:10,000 to 100:1.

A variety of homo-oligomerization or co-oligomerization conditions and combinations thereof may be employed, according to the starting materials, nature of the reaction (batch, semi-continuous, or continuous), apparatus set-up, desired products, and so forth. However, in general, suitable oligomers or co-oligomers of the invention may be produced using one or more of the specified catalyst selections at a temperature ranging from 20 degrees Celsius (° C.) to 220° C., and preferably 100° C. to 200° C., for a time preferably ranging from 10 minutes (min) to 300 min. Other parameters, such as pressure, may be controlled within ranges known to those skilled in the art and are not generally considered to be critical to practice of the present invention, but may be varied according to the desires and needs of the practitioner. It is usually preferred to carry out the process as a continuous process, using at least one continuous stir tank reactor (CSTR) or other suitable vessel(s).

The oligomerization process generates an oligomer (in some embodiments the hydrophobe) with a specific structure. In the desired fraction, the main carbon chain contains an average of preferably between 0.5 and 2.5 branches. The branches are predominantly (greater than 50%) ethyl branches, preferably greater than 80% ethyl branches. Finally, the branches are located more than one carbon away from each end of the main chain in more than 20% of the molecules on average, preferentially in more than 40% on average. Furthermore, the branches (on the oligomer) are situated at the C2 carbon (relative to the unsaturated chain end) in less than 40% of the molecules on average, preferably in less than 25% on average. Finally, the oligomer may contain a vinyl olefin, a vinylidene olefin, or a vinylene olefin. The oligomer product contains greater than 50% vinyl olefin, preferably greater than 70% vinyl olefin.

Figure 8:
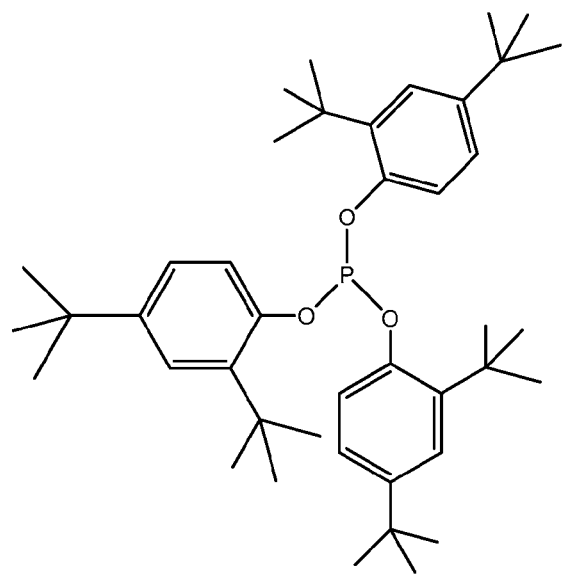
FIG. 8 is formula drawing of an organophosphorus ligand, tris(2,4-di-tert-butylphenyl) phosphite (L).

The preparation of the alcohol is carried out via hydroformylation followed by hydrogenation. Hydroformylation/hydrogenation to generate a primary alcohol may add more branching (i.e., a methyl branch at the C2 position relative to the alcohol) to the olefins oligomer with vinyl groups depending on the selectivity of the hydroformylation catalyst (i.e. whether hydroformylation occurs mostly at the C1 position of the olefin (little added branches relative to the corresponding olefin oligomer) or at the C2 position of the olefin (methyl branch introduced)). A rhodium catalyst with an organophosphorus ligand may be used for hydroformylation of the oligomer product. The organophosphorus ligand may be, for example, the one shown in FIG. 8 for tris(2,4-di-tert-butylphenyl) phosphite (L).

During hydroformylation, different types of olefins lead to various structures for related aldehydes. The aldehydes contain one carbon atom more than the starting olefins.

Subsequent hydrogenation of the aldehydes to the corresponding alcohols may be performed with hydrogen in the presence of a hydrogenation catalyst. For example, hydrogenation can be performed using platinum group metal catalysts or a nickel catalyst. The catalysts can be supported on activated carbon, silica or alumina or unsupported.

The alcohol product may comprise a main carbon chain containing an average of between 0.5 and 2.5 branches, wherein more than 50% of the branches are ethyl branches, wherein the branches are located more than one carbon away from each end of the main carbon chain in more than 20% of alcohol product molecules.

The process may further include the reaction of the alcohol with an alkylene oxide in the presence of a catalyst to generate nonionic alkoxylated surfactants. The alkylene oxide may be any epoxide with carbon numbers ranging from C2-C12. Preferably, the alkylene oxide is ethylene oxide, 1,2-epoxypropane, or 1,2-epoxybutane. Further, the alkoxylation step may involve alkoxylation of more than one type of alkylene oxide, as is known in the art. Also, each initiator may be alkoxylated by 1 to 100 alkylene oxide molecules, preferably by 1 to 20 alkylene oxide molecules, which may be all the same or a mixture of different alkylene oxides in a random or block configuration. The alkoxylation catalyst or catalyst precursor may be any catalyst known for alkoxylation reactions (as described in Alkylene Oxides and Their Polymers, Surfactant Science Series, Vol. 35, Ed. by F. E. Bailey, Jr. and Joseph V. Koleske, Marcel Dekker, Inc., New York, 1990). Preferred examples are alkali metal hydroxides, like sodium hydroxide, potassium hydroxide, alkali earth metal hydroxide, alkali metals, like sodium or potassium, potassium hydride, and DMC (double metal cyanide) catalysts. The alkoxylation reaction may be conducted in a solvent or without solvent. The solvent can be any solvent suitable for use in alkoxylation reactions. It is preferable that the solvent be capable of dissolving the reactants. Examples of solvents include dimethoxyethane, THF, 1,4-dioxane, diglyme, and tetraglyme.

The nonionic alkoxylated surfactants may further be sulfated to produce an anionic ether sulfate surfactant product. In an alternative embodiment, the alcohol may be sulfated to produce an anionic sulfate surfactant product.

In an alternative embodiment, instead of hydroformylating the oligomer olefin, the oligomer olefin may instead be sulfonated to generate anionic sulfonated surfactants. Due to the composition of the oligomer (i.e. vinyl, vinylidene and vinylene olefins), the product is a mixture of lightly branched alpha olefin sulfonates (AOS) and internal olefin sulfonates (IOS).

The final lightly branched surfactant product may comprise a main carbon chain containing an average of between 0.5 and 2.5 branches, wherein more than 50% of the branches are ethyl branches, wherein the branches are located more than one carbon away from each end of the main carbon chain in more than 20% of surfactant product molecules.

The final nonionic products (nonionic surfactants) should be able to reduce the surface tension of water. For a 0.1 wt % aqueous solution, the equilibrium surface tension should be less than 50 mN/m and the contact angle on a PTFE film should be less than 75 degrees. Further surfactant performance requirements may be obtained in other similar applications for nonionic and anionic surfactants.

Possible applications of the nonionic and anionic surfactants generated include household and industrial cleaning, personal care, paints & coatings, emulsion polymerization, agriculture, oil & gas, textile process, food processing, lubricant and fuel additives, leather processing and mining.

EXAMPLES

Various examples are demonstrated.

Example 1: Ethylene Oligomerization Catalyst Preparation

Analytical Measurements

For $^{13}$C NMR experiments, samples are dissolved in 10 mm NMR tubes in chloroform-d with 0.02 M Cr(acac)$_3$ added. The typical concentration is 0.50 g/2.4 mL. The tubes are then heated in a heating block set at 50° C. The sample tubes are repeatedly vortexed and heated to achieve a homogeneous flowing fluid. For samples with visible wax present, tetrachloroethane-d$_2$ is used as the solvent instead of chloroform-d, and the sample preparation temperature is 90° C.

$^{13}$C NMR spectra are taken on a Bruker Avance 400 MHz spectrometer equipped with a 10 mm cryoprobe. The following acquisition parameters are used: 5 seconds relaxation delay, 90 degree pulse of 13.1 μs, 256 scans. The spectra are centered at 80 ppm with a spectral width of 250 ppm. All measurements are taken without sample spinning at either 50° C. (for chloroform solutions) or 90° C. (for tetrachloroethane solutions). The $^{13}$C NMR spectra are referenced to 77.3 ppm for chloroform or 74.5 ppm for tetrachloroethane.

Catalyst Synthesis

Figure 9:
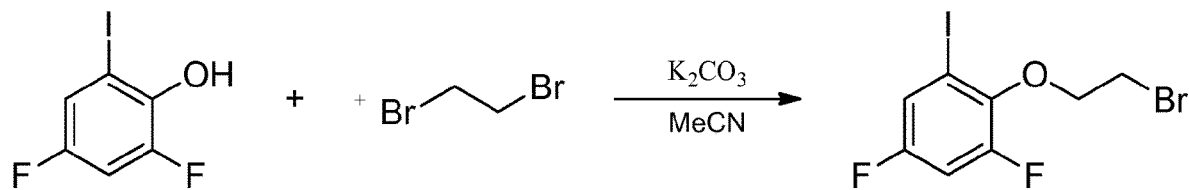
FIG. 9 is a reaction scheme for the preparation of 2-(2-bromoethoxy)-1,5-difluoro-3-iodobenzene.

Preparation of 2-(2-bromoethoxy)-1,5-difluoro-3-iodobenzene 16.55 g (64.65 mmol) of 2-iodo-4,6-difluorophenol, 86.232 g (459.02 mmol) of 1,2-dibromoethane, 29.5 g (213.35 mmol) of potassium carbonate and acetonitrile (85 mL) is place in a 250 mL round bottom flask. The reaction is shown in FIG. 9. The suspension is stirred at 60° C. under nitrogen overnight. The reaction is filtered and the organic solution is concentrated. The residue is run through a 220 g ISCO column eliminating one impurity and the remaining 1,2-dibromoethane. The product is 18.22 g of a colorless oil (77.6% Yield). $^1$H NMR (400 MHz, Chloroform-d) δ 7.30 (ddd, J=7.4, 3.0, 2.0 Hz, 1H), 6.89 (ddd, J=10.7, 8.1, 2.9 Hz, 1H), 4.34-4.29 (m, 2H), 3.70-3.65 (m, 2H). $^{13}$C NMR (101 MHz, cdcl$_3$) δ 159.63, 159.52, 157.03, 152.62, 121.06, 105.73, 91.48, 73.44, 73.40, 28.97. $^{19}$F NMR (376 MHz, Chloroform-d) δ −114.47 (tt, J=7.6, 3.4 Hz), −122.18 (dd, J=10.7, 3.0 Hz).

Figure 10:
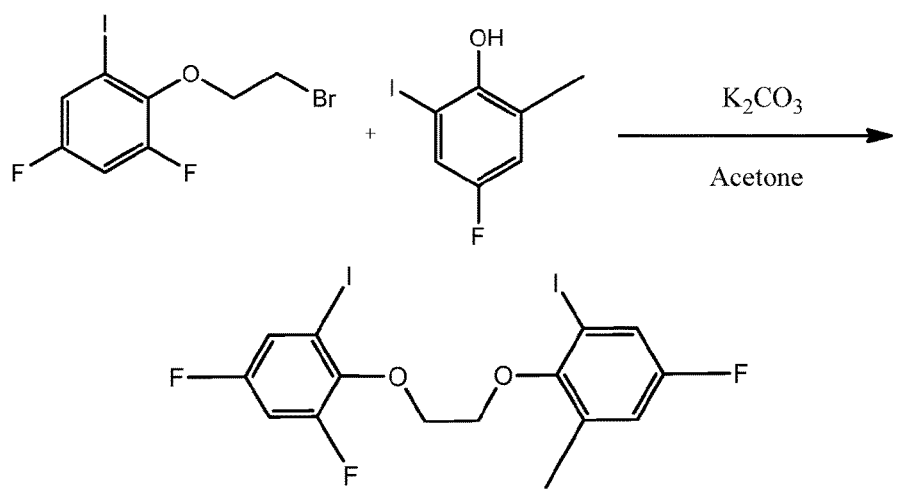
FIG. 10 is a reaction scheme for the preparation of 2-(2-(2,4-difluoro-6-iodophenoxy)ethoxy)-5-fluoro-1-iodo-3-methylbenzene.

Preparation of 2-(2-(2,4-difluoro-6-iodophenoxy)ethoxy)-5-fluoro-1-iodo-3-methylbenzene 150 mL of acetone, 3.768 g (27.261 mmol) of potassium carbonate, 6.00 g (16.036 mmol) of 1-(2-bromoethoxy)-2,4-difluorobenzene, and 4.041 g (16.036 mmol) of 2-iodo-4-fluoro-6-methylphenol is added to a 250 mL round bottom flask under nitrogen. The reaction is shown in FIG. 10. The solution is heated to reflux overnight. Gas chromatography (GC) confirms full conversion to product, so the reaction mixture is cooled, filtered and the filtrate was concentrated. The residue is dissolved in methylene chloride, washed with brine, dried over magnesium sulfate, and recrystallized from acetonitrile. The solid is then run through a 330 g ISCO column using a hexanes:ethyl acetate gradient. The oil is then recrystallized to yield 4.23 g of the product (49.4% Yield).

¹H NMR (400 MHz, Chloroform-d) δ 7.31 (ddt, J=7.4, 3.0, 2.2 Hz, 2H), 6.93-6.86 (m, 2H), 4.44 (ddd, J=6.0, 3.9, 1.0 Hz, 2H), 4.23 (ddd, J=5.5, 4.2, 0.6 Hz, 2H), 2.40 (s, 3H).
¹³C NMR (101 MHz, cdcl₃) δ 159.80, 159.44, 159.33, 157.34, 156.96, 156.84, 155.30, 155.18, 153.20, 153.17, 152.78, 152.65, 143.73, 143.69, 143.61, 143.57, 133.59, 133.50, 123.51, 123.27, 121.27, 121.23, 121.03, 120.99, 118.08, 117.85, 91.47, 91.44, 91.36, 91.34, 91.14, 91.05, 72.90, 72.86, 71.53, 17.45, 17.44.
¹⁹F NMR (376 MHz, Chloroform-d) δ −115.24 (td, J=7.7, 3.7 Hz), −117.55−−117.74 (m), −122.11 (dt, J=10.8, 2.7 Hz).

Figure 11:
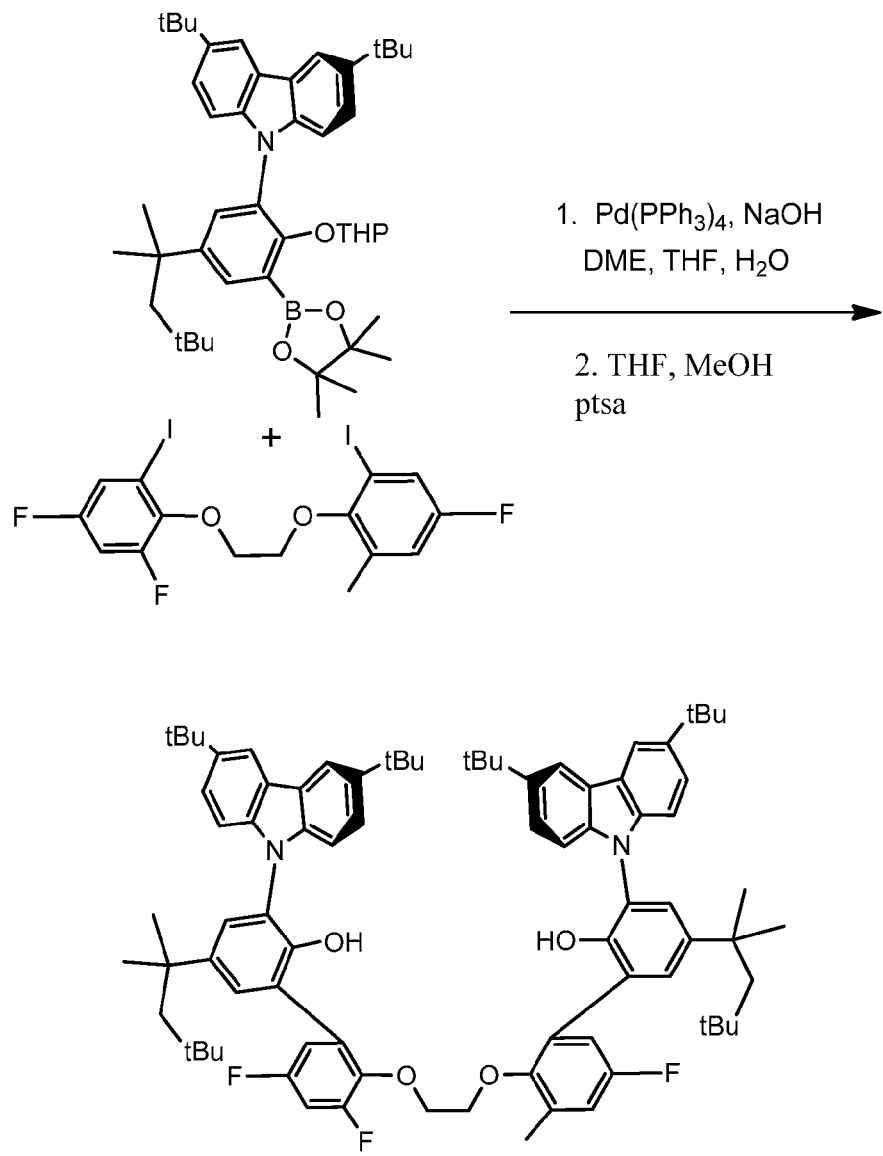
FIG. 11 is a reaction scheme for the preparation of 3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol.

Preparation of 3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol 1,2-dimethoxyethane (67 mL) is added to 4.00 g (5.725 mmol) of 3,6-di-tert-butyl-9-(2-(((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole, 1.482 g (2.719 mmol) of 2-(2-(2,4-difluoro-6-iodophenoxy)ethoxy)-5-fluoro-1-iodo-3-methylbenzene, a solution of NaOH (0.6870 g) in water (16 mL) and THF (40 mL) in a three neck 250 mL round bottom flask. The reaction is shown in FIG. 11. The reaction mixture is sparged with N₂ for 15 minutes then 0.1322 g (0.1145 mmol) of Pd(PPh₃)₄ is added. Upon addition the reaction mixture is heated to 85° C. overnight. The reaction mixture is then concentrated with the residue being taken up in methylene chloride (200 mL), washed with brine (200 mL), dried over anhydrous magnesium sulfate, filtered through a pad of silica gel, and concentrated to afford crude protected ligand. THF (50 mL), methanol (50 mL) and PTSA is added to the crude protected ligand until the solution is acidic. The solution is heated to 60° C. overnight, then cooled and concentrated. The crude ligand is taken up in methylene chloride (100 mL), washed with brine (100 mL), dried with anhydrous magnesium sulfate, filtered through a pad of silica gel then concentrated to afford ligand as an off white crystalline powder. Thin layer chromatography (TLC) shows impurities, so the ligand is run through a 330 g column using solid phase loading and a ethyl acetate: hexanes gradient. The appropriate fractions are concentrated and placed under vacuum overnight to afford 2.7 g of white crystals (79.7% Yield).
¹H NMR (400 MHz, Chloroform-d) δ 8.14 (d, J=7.7 Hz, 4H), 7.43-7.16 (m, 9H), 7.06-6.79 (m, 8H), 6.06 (d, J=1.7 Hz, 1H), 5.58 (d, J=1.9 Hz, 1H), 4.04 (t, J=4.8 Hz, 2H), 3.78 (t, J=4.8 Hz, 2H), 2.04 (d, J=1.8 Hz, 3H), 1.70-1.63 (m, 4H), 1.44 (dd, J=8.6, 1.7 Hz, 36H), 1.28 (d, J=27.3 Hz, 12H), 0.75 (s, 16H).
¹³C NMR (101 MHz, CDCl₃) δ 160.25, 159.14, 157.83, 156.82, 156.75, 156.70, 156.62, 149.78, 149.76, 147.60, 147.42, 143.33, 143.30, 143.13, 143.03, 142.55, 140.46, 140.43, 140.35, 140.31, 139.68, 139.43, 139.40, 134.36, 134.33, 134.26, 134.23, 133.94, 133.86, 133.04, 132.95, 128.78, 128.74, 127.52, 127.28, 126.17, 126.15, 125.42, 124.96, 124.93, 124.91, 124.68, 124.05, 123.74, 123.60, 123.56, 123.53, 123.40, 117.39, 117.17, 116.43, 116.35, 116.10, 115.87, 113.65, 113.62, 113.41, 109.32, 109.26, 104.73, 104.47, 104.24, 72.74, 72.70, 72.26, 57.03, 56.95, 38.22, 38.20, 34.74, 32.44, 32.42, 32.14, 32.05, 31.93, 31.87, 31.69, 31.62, 31.52, 31.46, 30.38, 16.39.
¹⁹F NMR (376 MHz, Chloroform-d) δ −115.26 (dt, J=8.7, 4.1 Hz), −117.94 (t, J=8.7 Hz), −124.48 (dd, J=11.1, 4.2 Hz).

Figure 12:
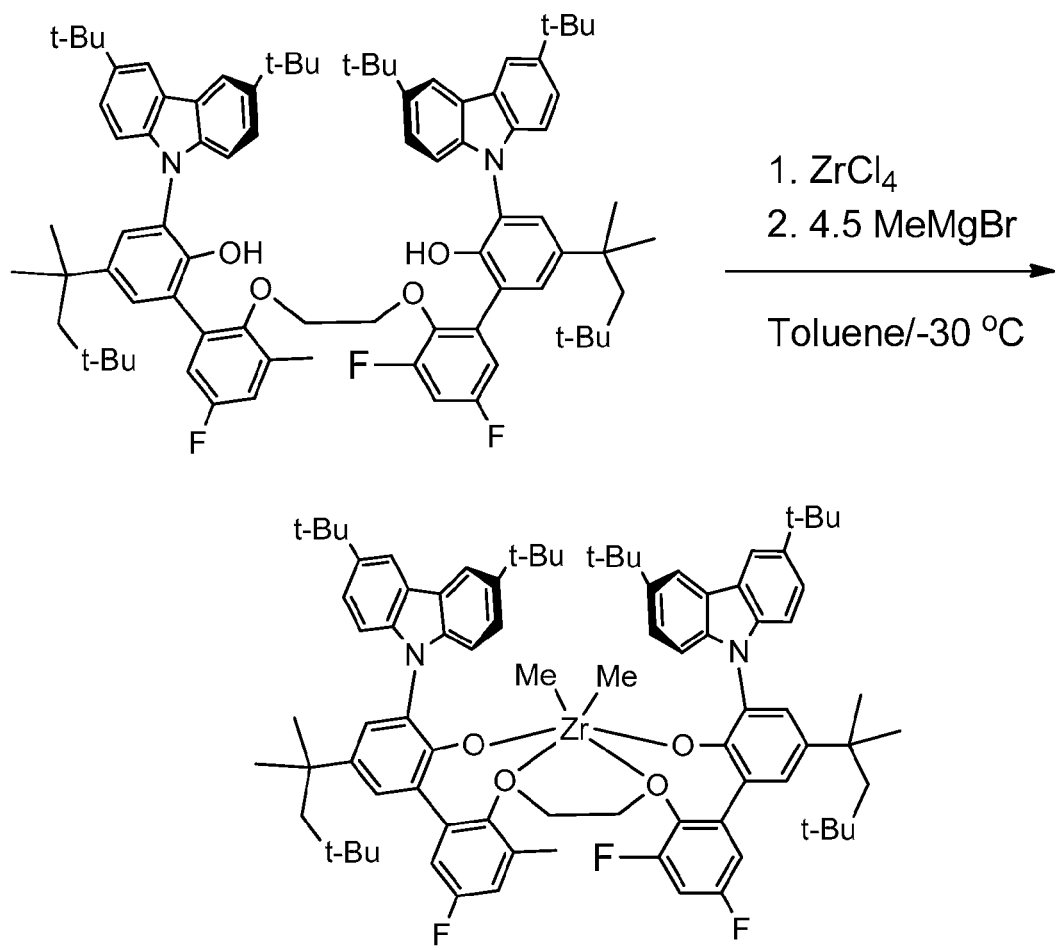
FIG. 12 is a reaction scheme for the preparation of (3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol)dimethyl-zirconium.

Preparation of (3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol)dimethyl-zirconium A 20 mL vial is charged with ZrCl₄ (0.119 g, 0.509 mmol) and toluene (10 mL) and cooled to −35° C. MeMgBr (3M solution in ether, 0.66 mL, 1.98 mmol) is added to the solution. The reaction is shown in FIG. 12. The solution quickly turns to a dark color. After 5 min of stirring the solution is treated with a −35° C. toluene (7 mL) solution of 3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol (0.615 g, 0.494 mmol). The solution is allowed to stir for 3 hours, then the solution is passed through a filter frit. The solids are washed with toluene and all volatiles are removed in vacuo leaving a white solid. The white solid is dissolved in hexanes and passed through a 0.45 micron frit. All volatiles are removed and the crude solid is checked by ¹H NMR and used without further purification. Yield 91% (0.610 g).
¹H NMR (400 MHz, C₆D₆) δ 8.21-8.40 (m, 4H), 7.96-8.00 (m, 1H), 7.85 (d, 1H), 7.61-7.72 (m, 3H), 7.48-7.50 (m, 2H), 7.28-7.34 (m, 3H), 7.17 (d, 1H), 6.86-7.10 (m, 3H), 6.65-6.68 (m, 1H), 6.19-6.22 (m, 1H), 3.76-3.77 (m, 2H), 2.65-2.73 (m, 2H), 1.54-1.62 (m, 4H), 1.50 (s, 9H), 1.49 (s, 9H), 1.35 (s, 9H), 1.31 (s, 9H), 1.18-1.29 (m, 12H), 0.99 (s, 3H), 0.80 (s, 9H), 0.76 (s, 9H), −0.76 (s, 3H), −0.96 (s, 3H).
¹³C{¹H} NMR (101 MHz, C₆D₆) δ 155.9, 155.6 (d), 153.4, 153.1 (d), 148.5 (d), 148.1, 147.1, 142.1 (d), 137.4, 137.1, 136.9, 136.6, 135.7, 135.6, 134.6, 134.2, 134.1 (d), 134.0, 131.1 (dd), 130.9 (d), 123.9, 123.8, 123.0, 122.9, 121.5, 121.3, 120.1, 119.4, 119.3, 119.2, 118.3, 118.2, 117.0, 117.1, 112.6, 112.3, 111.5, 111.5, 111.2, 111.0, 110.5 (d), 108.7, 108.5, 107.6 (d), 105.5 (d), 103.9, 97.9 (d), 97.6 (d), 64.7, 64.6, 52.0, 51.7, 37.4, 36.4, 36.3, 32.9, 32.8, 29.5, 29.5, 29.4, 29.3, 27.1, 27.1, 27.0, 26.9, 26.9, 26.8, 26.7, 26.6, 26.5, 25.7 (br m), 17.5, 10.4, 8.9.
¹⁹F NMR (376 MHz, C₆D₆) δ −110.55 (m), −115.33 (m), −119.54 (m).

Example 2: Ethylene Oligomerization

Semi-Batch Oligomerizations

Oligomerizations are conducted in a 2 L Parr™ batch reactor. The reactor is heated by an electrical heating mantle, and is cooled by an internal serpentine cooling coil containing cooling water. Both the reactor and the heating/cooling system are controlled and monitored by a Camile™ TG process computer. The bottom of the reactor is fitted with a dump valve, which empties the reactor contents into a stainless steel dump pot, which is prefilled with a catalyst kill solution (typically 5 mL of an Irgafos™/Irganox™/toluene mixture).

The dump pot is vented to a 30 gallon blowdown tank, with both the pot and the tank N₂ purged. All chemicals used for oligomerization or catalyst makeup are run through purification columns to remove any impurities that may affect oligomerization. Liquid feeds such as alpha-olefin and solvents are passed through two columns, the first containing $Al_2O_3$ alumina, the second containing Q5, which is a copper reactant to scrub oxygen. Ethylene feed is passed through two columns, the first containing $Al_2O_3$ alumina and 4 Angstroms (Å) average pore size molecular sieves to remove water, the second containing Q5 reactant. The $N_2$, used for transfers, is passed through a single column containing $Al_2O_3$ alumina, 4 Å average pore size molecular sieves, and Q5 reactant.

The reactor is loaded first from the shot tank containing toluene. The shot tank is filled to the load set points by use of a lab scale to which the shot tank is mounted. After liquid feed addition, the reactor is heated up to the polymerization temperature set point. Ethylene is added to the reactor when at reaction temperature to maintain reaction pressure set point. Ethylene addition amounts are monitored by a micromotion flow meter and integrated to give overall ethylene uptake after catalyst injection.

The catalyst and bis (octadecyl)methylammonium tetrakis (pentafluorophenyl) borate ($[HNMe(C_{18}H_{37})_2][B(C_6F_5)_4]$) (BOMATPB) activator are mixed with the appropriate amount of purified toluene to achieve a desired molarity solution. The catalyst and activator are handled in an inert glove box, drawn into a syringe and pressure transferred into the catalyst shot tank. This is followed by three rinses of toluene, 5 mL each. Immediately after catalyst addition the run timer begins. Ethylene is then added continuously by the Camile™ to maintain reaction pressure set point in the reactor. If the ethylene uptake rate is low, then the headspace is purged, more catalyst and activator are added, and the ethylene pressure is re-established. After a designated time or ethylene uptake the agitator is stopped and the bottom dump valve opened to empty reactor contents to the dump pot. The dump pot contents are poured into a round bottom flask and all C8 and below volatiles were removed via rotary evaporation (80° C./20 Torr).

Example 3: Fractionation

A Vigreux column and short path distillation head are equipped onto the round bottom flask and the crude product is first distilled at 50° C./500 mTorr to remove the ~C10 components. Next, the heating bath is raised to 100° C. (300 mTorr) and the ~C12 fractions are collected, followed by the ~C14 fractions at 135° C. (200 mTorr). The Vigreux column is then removed and the ~C16 fractions can be collected at 100° C./100 mTorr. Distillation of the desired products may be done at various temperature/pressures and those skilled in the art will recognize the importance of theoretical plates on the degree of separation.

A series of semibatch oligomerizations are performed with 3-(3,6-di-tert-butyl-9H-carbazol-9-yl)-2'-(2-((3'-(3,6-di-tert-butyl-9H-carbazol-9-yl)-3,5-difluoro-2'-hydroxy-5'-(2,4,4-trimethylpentan-2-yl)-[1,1'-biphenyl]-2-yl)oxy)ethoxy)-5'-fluoro-3'-methyl-5-(2,4,4-trimethylpentan-2-yl)-[1,1'-biphenyl]-2-ol-zirconiumdimethyl (Formula (VI)) catalyst at 60° using toluene as a reaction solvent (Table 1 below). The semibatch nature of the reaction is due to the continuous feeding of ethylene gas to maintain a constant pressure, and excess butene is purged out to allow the continued consumption of ethylene. No alpha-olefin comonomers are added to the reaction. The average number of carbons per product oligomer is calculated assuming all molecules have a single unsaturation group.

TABLE 1

| Run # | Temp (*C) | Toluene (g) | Press (psi) | Run Time (min) | Catalyst Name | μmoles | Metal | RIBS-2 μmoles | MMAO-3A μmoles | Exo-Therm (*C) | Ethylene Initial (g) | Ethylene Added (g) |
|---|---|---|---|---|---|---|---|---|---|---|---|---|
| 1 | 60 | 300 | 116 | 164.6 | Formula VI | 16.9 | Zr | 20.28 | 10 | 7.6 | 21.6 | 120 |
| 2 | 60 | 300 | 116 | 226.9 | Formula VI | 39.9 | Zr | 39.9 | 10 | 2.2 | 19.4 | 220.6 |

TABLE 2

| | Average MW Mn | Average # of branches (per chain) | Detailed Degree of branching (Including chain ends) | | | | Conc. of unsaturation (per chain) | | | | Branching position (relative to unsat. Chain ends) | |
|---|---|---|---|---|---|---|---|---|---|---|---|---|
| | | | Hexyl | Butyl | Ethyl | Methyl | Vinylene | Vinyl V1 | V3 | Vinylidene | C2 | C4 |
| C12 fraction - Run #1 | 167 | 0.80 | 0.66 | 0.29 | 0.86 | 0.01 | 0.03 | 0.39 | 0.43 | 0.17 | 17% | 42% |
| C14 fraction - Run #1 | 185 | 0.91 | 0.66 | 0.33 | 0.96 | 0.01 | 0.03 | 0.35 | 0.45 | 0.17 | 17% | 45% |
| C16 fraction - Run #1 | 216 | 1.12 | 0.70 | 0.39 | 1.12 | 0.01 | 0.04 | 0.30 | 0.46 | 0.17 | 17% | 48% |
| C12 fraction - Run #2 | 164 | 0.82 | 0.63 | 0.31 | 0.88 | 0.01 | 0.03 | 0.37 | 0.43 | 0.19 | 18% | 42% |
| C14 fraction - Run #2 | 180 | 0.91 | 0.63 | 0.33 | 0.98 | 0.01 | 0.03 | 0.33 | 0.45 | 0.19 | 19% | 45% |
| C16 fraction - Run #2 | 210 | 1.10 | 0.70 | 0.38 | 1.08 | 0.01 | 0.04 | 0.31 | 0.46 | 0.19 | 19% | 46% |

Determination of the characterizing properties listed above in Table 2 may be accomplished as follows:

For $^{13}$C NMR measurement, product samples are dissolved in 10 millimeter (mm) nuclear magnetic resonance (NMR) tubes in chloroform-d$_1$ (deuterated chloroform) to which 0.02 molar (M) chromium acetylacetonate, Cr(acac)$_3$, is added. The typical concentration is 0.50 grams per 2.4 milliliter (g/mL). The tubes are then heated in a heating block set at 50° C. The sample tubes are repeatedly vortexed and heated to achieve a homogeneous flowing fluid. For samples with visible wax present, tetrachloroethane-d$_2$ (deuterated tetrachloroethane) is used as the solvent instead of chloroform-d$_1$, and the sample preparation temperature is 90° C. $^{13}$C NMR spectra are taken on a Bruker Avance 400 megaherz (MHz) spectrophotometer equipped with a 10 mm cryoprobe. The following acquisition parameters are used: 5 seconds relaxation delay, 90 degree pulse of 13.1 milliseconds, 256 scans. The spectra are centered at 80 parts per million (ppm) with a spectral width of 250 ppm. All measurements are taken without sample spinning at either 50° C. (for chloroform-d$_1$ solutions) or 90° C. (for tetrachloroethane-d$_2$ solutions). The $^{13}$C NMR spectra are referenced to 77.3 ppm for chloroform-d$_1$ or 74.5 ppm for tetrachloroethane-d$_2$.

Example 4: Hydroformylation of C12 Olefins to C13 Aldehydes

Rh(CO)$_2$(acac) (15.1 mg; 0.0585 mmol), tris(2,4-di-tert-butylphenyl)phosphite (757 mg; 1.17 mmol) and toluene (20 g) are placed in a 50 mL nitrogen purged bottle with a septum. The mixture is stirred until the components dissolved to form a yellow solution. The solution is transferred by syringe into a 150 mL Parr reactor under nitrogen, then purged three times with syngas (1:1) at 100 μsi with stirring and activated at 90° C. and 100 μsi of syngas (1:1) for about 1 h. Then the syngas is vented and the starting C12 olefin feedstock (9.39 g) is quickly added to the reactor via syringe. The reaction is carried out for two hours at 100° C. and then analyzed by $^1$H NMR. The olefin signals at about 2 ppm and 4.5-6 ppm disappeared and new signals of aldehyde protons appeared at 9.5-10 ppm, suggesting that the reaction is complete. Toluene is removed under reduced pressure and the aldehydes are separated from the catalyst and the ligand by vacuum distillation at 57° C./127 mm Hg to give 7.46 g of the aldehyde product.

Example 5: Hydrogenation of the C13 Aldehydes

A distilled aldehyde product from the previous example (7.46 g) is dissolved in 20 mL of anhydrous THF and hydrogenated in a 150 mL Parr reactor at 500 psi and 100° C. using 0.75 g of 5% Ru/C catalyst from Strem Chemical. The reaction is followed by hydrogen pressure drop. $^1$H NMR analysis indicates in four hours that no residual aldehyde remains. The mixture is filtered, the catalyst washed with 5 mL×2 of THF and the combined solutions are evaporated in vacuum to give 7.18 g of the alcohol product.

Example 6: Hydroformylation of C14 Olefins to C15 Aldehydes

Rh(CO)$_2$(acac) (25.0 mg; 0.0969 mmol), tris(2,4-di-tert-butylphenyl)phosphite (1.161 g; 1.79 mmol) and toluene (20 g) are placed in a 50 mL nitrogen purged bottle with a septum. The mixture is stirred until the components dissolved to form a yellow solution. The solution is transferred by syringe into a 150 mL Parr reactor under nitrogen, then purged three times with syngas (1:1) at 100 μsi with stirring and activated at 90° C. and 100 psi of syngas (1:1) for about one hour. Then the syngas is vented and the starting C14 olefin feedstock (15.03 g) is quickly added to the reactor via syringe. The reaction is carried out for two hours at 100° C. and then analyzed by $^1$H NMR. The olefin signals at about 2 ppm and 4.5-6 ppm disappear and new signals of aldehyde protons appear at 9.5-10 ppm, suggesting that the reaction is complete. Toluene is removed under reduced pressure and the aldehydes are separated from the catalyst and the ligand by vacuum distillation at 68° C./202 mm Hg to give 11.99 g of the aldehyde product.

Example 7: Hydrogenation of the C15 Aldehydes

A distilled aldehyde product from the previous example (11.99 g) is dissolved in 50 mL of anhydrous THF and hydrogenated in a 150 mL Parr reactor at 500 μsi and 100° C. using 1.2 g of 5% Ru/C catalyst from Strem Chemical. The reaction is followed by hydrogen pressure drop. $^1$H NMR analysis indicates in four hours that no residual aldehyde remains. The mixture is filtered, the catalyst washed with 10 mL×2 of THF and the combined solutions are evaporated in vacuum to give 11.80 g of the alcohol product. The characterizing properties of the C13 and C15 alcohol products are listed below in Table 3.

TABLE 3

| | Average MW Mn | Average # of branches (per chain) | Detailed Degree of branching (Including chain ends) | | | | | Branching position (relative to hydroxyl group) | | | C2 | |
|---|---|---|---|---|---|---|---|---|---|---|---|---|---|
| | | | Methyl | Ethyl | Propyl | Butyl | Longer | Quarternary | >=C4 | C3 | Methyl | Ethyl | Longer |
| | | | | | (per chain) | | | | | | | | |
| C13 Alcohol | 175 | 1.27 | 0.17 | 0.32 | 0.05 | 0.21 | 0.26 | 0.0 | 41% | 6% | 36% | 6% | 12% |
| C15 Alcohol | 203 | 1.58 | 0.14 | 0.29 | 0.08 | 0.22 | 0.27 | 0.0 | 38% | 4% | 33% | 6% | 19% |

Example 8: Ethoxylation of the C13 and C15 Alcohols

The reactions are carried out in a Symyx PPR® (Parallel Pressure Reactor) setup using twelve small reactors. The MFRM-331448 library involves ethoxylation of the alcohols with ethylene oxide (EO). The library layout was designed using Library Studio®.

Ethylene oxide (EO) is delivered via an Isco syringe pump equipped with a robotically controlled needle and compressed gas micro-valve connected to the Symyx PPR®. Glass inserts along with removable PEEK stir paddles for each of twelve cells are dried in a vacuum oven at 125° C. overnight. The starter solutions after dissolution of potassium (1 wt %) are charged manually into the glass inserts under nitrogen using a pipette. The amounts of starting alcohols are 4 mmol for all cases (Table 3).

All reagents are delivered by pipette into glass inserts and the mass of material in each inset is recorded. The inserts with reagents are loaded into the corresponding PPR wells, the reactor modules are sealed, heated to 60° C., and pressurized with 50 µsi nitrogen. The corresponding twelve cells are charged with calculated amounts of EO. The temperature is then increased to 150° C. and the reaction mixtures are stirred for three hours at that temperature. The reactors are then cooled, and the cells are vented and purged with nitrogen to remove residual EO. After cooling to room temperature, the glass inserts are removed from the reactors, the weights of the glass inserts are taken, and the product yields are calculated. The materials are analyzed by $^1$H NMR and the number of EO equivalents for each product are determined (Table 4).

TABLE 4

| Sample | Average Number of carbons in ROH | ROH weight (g) | EO added (g) | Product yield (g) | EO equiv by $^1$H NMR |
|---|---|---|---|---|---|
| 1 | C13 | 0.813 | 0.805 | 1.616 | 4.9 |
| 2 | C13 | 0.813 | 1.283 | 2.094 | 6.8 |
| 3 | C13 | 0.813 | 2.289 | 3.100 | 14.6 |
| 4 | C15 | 0.925 | 1.098 | 2.023 | 7.0 |
| 5 | C15 | 0.925 | 1.710 | 2.635 | 10.1 |
| 6 | C15 | 0.925 | 2.332 | 3.257 | 14.3 |

Example 9: Surface Properties of Surfactants

Surface Tension

The surface tension of a surfactant solution is measured using Kruss K100 Surface Tensiometer fitted with a Wilhelmy platinum plate at ambient temperature (21-22° C.). Deionized water is used to make the solutions and the surface tension of the water is measured to be between 72 and 73 mN/m. The result is reported as a mean of five repeated testing values with the standard deviation <0.1 mN/m.

Ross-Miles Foam Test

Ross-Miles Foam test is conducted as described by ASTM method D1173 "Standard Test Method for Foaming properties of Surface Active Agents." A glass pipet ("foam pipet") is charged with 200 ml of the 0.1% aqueous surfactant solution, while the graduated glass tube ("foam receiver") with ID=5.0 cm is filled with 50 ml of the same solution. After centering the pipet above the foam receiver, the aqueous solution in the pipet is allowed to drain 90 cm through air and splash into the solution in the foam receiver, thereby forming foam. The height of the foam layer, a measure of the volume of air which is incorporated into the foam, was recorded at zero seconds, and at five minutes. Two measurements are made for each system at the ambient temperature and result is reported as the mean.

Draves Wetting Time

Draves Wetting time is tested following the procedures of ASTM D 2281-68 (Standard Test Method for Evaluation of Wetting Agents by the Skein Test). All the tests are carried out at 0.1 weight percent concentration of surfactant and at room temperature.

Contact Angle

Contact angle measurements are performed at ambient temperature utilizing Kruss DSA-100 Drop Shape Analyzer. The instrument has a movable sample stage. Kruss software, DSA3.exe, controlled operation of the instrument and performed data analysis. The contact angle measurements is performed on a static sessile (i.e. sitting) drop. Teflon® tape (pink thread seal tape purchased from Lowes) or parafilm is carefully placed on glass microscope slide, using a small amount of adhesive on the each edge of the microscope slide to hold the Teflon tape on the surface. Variability in surface composition and uniformity can significantly affect the contact angle measurement, thus, extreme care is used when placing tape on a slide so that the tape, film, or paper is not stretched or touched. The substrate was placed on a sample stage, and five liquid drops are deposited on the substrate programmatically, using the procedure predefined via DSA software. An automated procedure is utilized, as the drop volume, dispense rate, and needle height can affect the drop shape, and thus, the contact angle measurement. In this study, drop volume was 5 µL, rate of drop deposition was 6 µL/min, and measurement was made immediately after drop placement. Once the drop image is taken, the baseline is determined, left and right contact angles are determined by software, and the arithmetic mean of left and right contact angles is calculated for each drop. The result is reported as mean of the values from three groups of testing total fifteen drops.

The test results are summarized in Table 5 below. Two commercial products, Lutensol AO-7 (7 EO adduct of C13-C15 oxo alcohol) and Lutensol TO-7 (7EO adduct of iso-tridecanol) from BASF are included for comparison. The experimental samples demonstrate good surfactancy, reducing surface tension to about 30 mN/m with cmc lower than 100 ppm. Sample 1, which has similar amount EO adduction as the two commercial products, shows almost identical surface tension as the two commercial products, and demonstrates better wetting than Lutensol AO-7 and similar to Lutensol TO-7, a highly branched alcohol with low biodegradability.

TABLE 5

| Sample | ST cmc (ppm) | ST (0.1 wt %) mN/m | Ross Miles Foam (0.1 wt %) 0 min. | Ross Miles Foam (0.1 wt %) 5 min. | Draves Wetting (0.1 wt %) (sec.) | Contact angle (degree) PTFE | Contact angle (degree) Parafilm |
|---|---|---|---|---|---|---|---|
| 1 - C13 | 36 | 28.2 | 30 | 30 | 26 | 59 | 50 |
| 2 - C13 | 35 | 27.8 | 110 | 110 | 18 | 55 | 49 |
| 3 - C13 | 96 | 31.4 | 128 | 120 | 188 | 83 | 71 |
| 4 - C15 | 10 | 28.8 | 80 | 80 | 56 | 63 | 61 |
| 5 - C15 | 10 | 30.4 | 110 | 110 | 70 | 70 | 64 |
| 6 - C15 | 17 | 33.4 | 120 | 120 | 228 | 77 | 72 |
| Lutensol AO-7 | 6 | 27.9 | 85 | 85 | 47 | 62 | 58 |
| Lutensol TO-7 | 19 | 27.3 | 65 | 60 | 13 | 53 | 46 |

Example 10: Biodegradability Test of the Surfactant Samples

The ready biodegradability of the Experimental surfactant samples is evaluated using the OECD guideline 301F: Manometric Respirometry test. Biodegradation of each material is determined at an initial concentration of approximately 50 mg/L, yielding approximately 100 mg/L theoretical oxygen demand (ThOD) in the test mixtures. The test chemicals are added to biodegradation test mixtures containing a defined mineral medium, which is inoculated with activated sludge (30 mg/L dry solids) from a municipal wastewater treatment facility (Midland, Mich. USA). This facility treats an excess of 11 million L/day of a predominantly domestic (>90% vol.) wastewater. Oxygen consumption and CO2 evolution resulting from biodegradation of the test chemicals are measured over twenty-eight days using a Columbus Instruments MicroOxymax® respirometer system. In addition, removal of dissolved organic carbon (DOC) from the biodegradation test mixtures is determined after twenty-eight days. The results are reported as below.

Sample 6:
88% Biodegradation by biological oxygen demand (BOD), 72% biodegradation by CO2 evolution, 95% by dissolved organic carbon (DOC) removal
Conclusion: Readily biodegradable Sample 1:
60% by BOD, 46% by CO2, and 97% by DOC
Conclusion: Readily biodegradable Sample 3:
100% by BOD, 81% by CO2, and 100% by DOC
Conclusion: Readily biodegradable While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:
1. A process for preparing an alcohol product comprising:
(1) combining at least one olefin and at least one coordination-insertion catalyst and, optionally, an alpha-olefin,
wherein the coordination-insertion catalyst is selected from the group consisting of

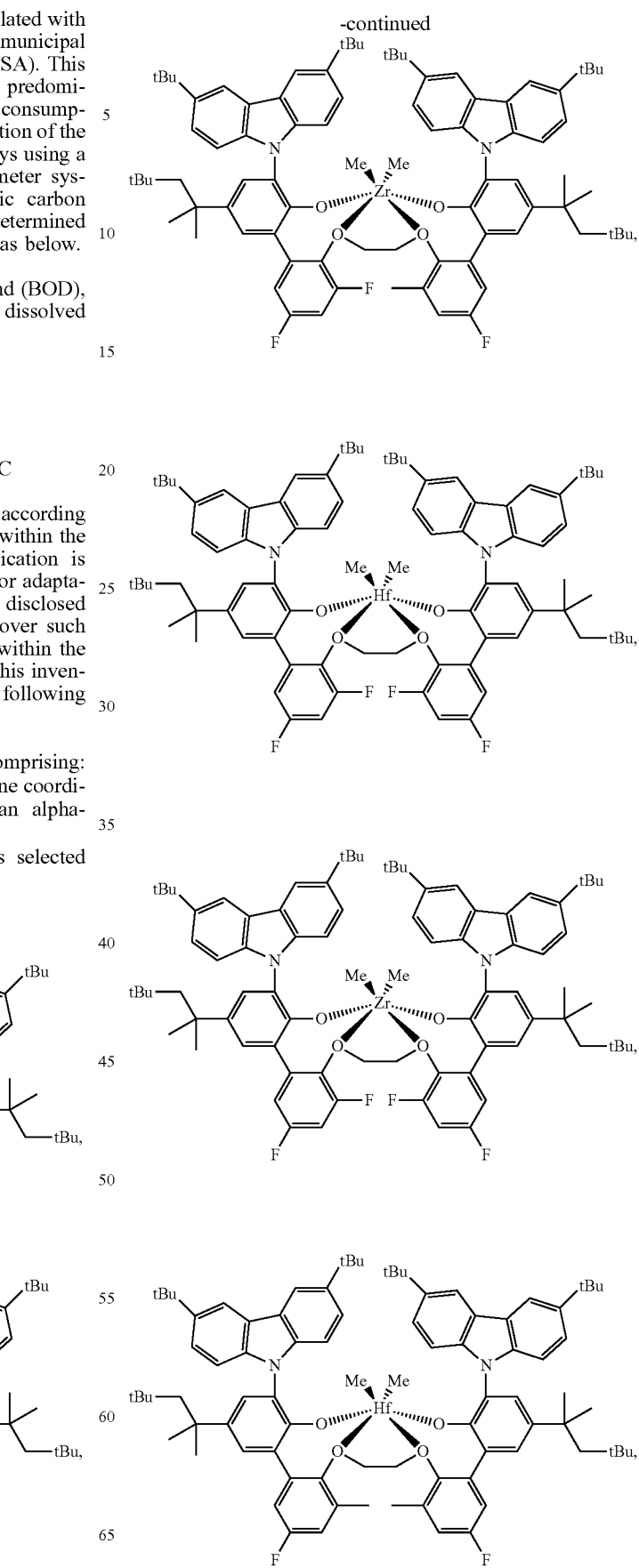

-continued

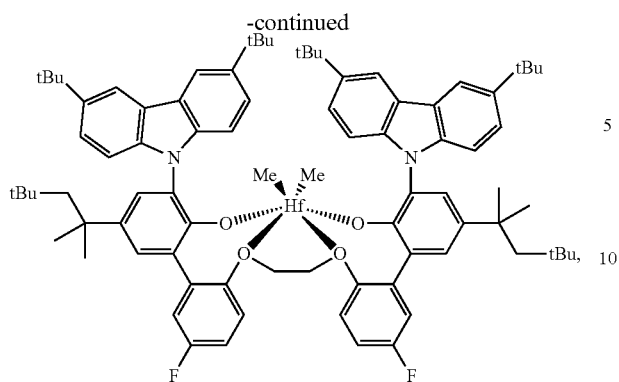

and combinations thereof,
and has an ethylene/octene reactivity ratio up to 20 at an operating reactor temperature, and a kinetic chain length up to 20 monomer units;
under conditions such that at least one oligomer product is formed,
wherein the oligomer product includes a main carbon chain containing an average of between 0.5 and 2.5 branches, wherein more than 50% of the branches are ethyl branches, wherein the branches are located on average more than one carbon away from each end of the main carbon chain in more than 20% of oligomer product molecules, wherein the branches are situated at a second carbon relative to an unsaturated end of the main carbon chain in less than 40% of the oligomer product molecules, and wherein the oligomer product contains greater than 50% vinyl olefin;
(2) fractionating the oligomer product to produce a fractionated oligomer product, such that the average carbon number of the fractionated oligomer product is between 8 and 28;
(3) hydroformylating the fractionated oligomer product to produce an aldehyde product; and
(4) hydrogenating the aldehyde product to produce the alcohol product.

2. A process according to claim 1, further comprising alkoxylating the alcohol product to produce an alkoxylate surfactant product.

3. A process according to claim 2, further comprising sulfating the alkoxylate surfactant product to produce an anionic ether sulfate surfactant product.

4. A process according to claim 1, further comprising sulfating the alcohol product to produce an anionic sulfate surfactant product.

5. A process according to claim 1, wherein the at least one olefin is ethylene and an alpha-olefin is not used.

6. A process according to claim 1, wherein the at least one olefin is an olefin mixture.

7. A process according to claim 6, wherein the olefin mixture includes olefins with vinyl groups, olefins with vinylidene groups, and olefins with vinylene groups.

8. A process according to claim 1, further comprising use of a rhodium catalyst with an organophosphorus ligand in the hydroformylating step (3).

9. A process for preparing an alcohol product comprising:
(1) combining at least one olefin and at least one coordination-insertion catalyst and, optionally, an alpha-olefin,
wherein the coordination-insertion catalyst is a metal-ligand complex of formula

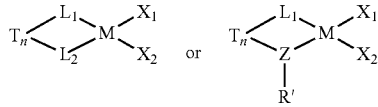

wherein M is the metal center, and is a Group 4 metal selected from titanium, zirconium or hafnium;
T is an optional bridging group which, if present is selected from dialkylsilyl, diarylsilyl, dialkylmethyl, ethylenyl (—$CH_2$—$CH_2$—) or hydrocarbylethylenyl wherein one, two, three or four of the hydrogen atoms in ethylenyl are substituted by hydrocarbyl, where hydrocarbyl can be independently $C_1$ to $C_{16}$ alkyl or phenyl, tolyl, or xylyl, and when T is present, the catalyst represented can be in a racemic or a meso form;
$L_1$ and $L_2$ are the same or different cyclopentadienyl, indenyl, tetrahydroindenyl or fluorenyl rings, optionally substituted, that are each bonded to M, or $L_1$ and $L_2$ are the same or different cyclopentadienyl, indenyl, tetrahydroindenyl or fluorenyl, which are optionally substituted;
Z is nitrogen, oxygen or phosphorus;
R' is a cyclic linear or branched $C_1$ to $C_{40}$ alkyl or substituted alkyl group; and
$X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from 3 to 20 carbon atoms; or both together can be an olefin, diolefin or aryne ligand,
and has an ethylene/octene reactivity ratio up to 20 at an operating reactor temperature, and a kinetic chain length up to 20 monomer units;
under conditions such that at least one oligomer product is formed,
wherein the oligomer product includes a main carbon chain containing an average of between 0.5 and 2.5 branches, wherein more than 50% of the branches are ethyl branches, wherein the branches are located on average more than one carbon away from each end of the main carbon chain in more than 20% of oligomer product molecules, wherein the branches are situated at a second carbon relative to an unsaturated end of the main carbon chain in less than 40% of the oligomer product molecules, and wherein the oligomer product contains greater than 50% vinyl olefin;
(2) fractionating the oligomer product to produce a fractionated oligomer product, such that the average carbon number of the fractionated oligomer product is between 8 and 28;
(3) hydroformylating the fractionated oligomer product to produce an aldehyde product; and
(4) hydrogenating the aldehyde product to produce the alcohol product.

10. A process according to claim 9, further comprising alkoxylating the alcohol product to produce an alkoxylate surfactant product.

11. A process according to claim 10, further comprising sulfating the alkoxylate surfactant product to produce an anionic ether sulfate surfactant product.

12. A process according to claim 9, further comprising sulfating the alcohol product to produce an anionic sulfate surfactant product.

13. A process according to claim 9, wherein the at least one olefin is ethylene and an alpha-olefin is not used.

14. A process according to claim 9, wherein the at least one olefin is an olefin mixture.

15. A process according to claim 14, wherein the olefin mixture includes olefins with vinyl groups, olefins with vinylidene groups, and olefins with vinylene groups.

16. A process according to claim 9, further comprising use of a rhodium catalyst with an organophosphorus ligand in the hydroformylating step (3).

* * * * *